United States Patent [19]

Brown

[11] Patent Number: Plant 7,440

[45] Date of Patent: Feb. 5, 1991

[54] AGLAONEMA PLANT NAMED REMBRANDT

[75] Inventor: B. Frank Brown, Palm Bay, Fla.

[73] Assignee: Hartman Plant Laboratories, Inc., Sebring, Fla.

[21] Appl. No.: 375,602

[22] Filed: Jul. 5, 1989

[51] Int. Cl.[5] ..... A01H 5/00

[52] U.S. Cl. ..... Plt./88

[58] Field of Search ..... Plt./88

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A new and distinct cultivar of Aglaonema plant named 'Rembrandt' characterized by its unique leaf coloring comprised of dark green and gray-green stripes, and yellow spots and midribs, pink petioles, free branching resulting in a wide appearance, relatively large leaves, and short underground stolons.

1 Drawing Sheet

The present invention comprises a new and distinct cultivar of Aglaonema hybrida known by the cultivar name 'Rembrandt'.

The new cultivar is a product of a planned breeding program carried out by the inventor B. Frank Brown in Palm Bay, Fla. The parents of the new cultivar are Aglaonema, 'Manilla Twirl' (seed parent) and an unnamed cultivar of *Aglaonema panayensis* (pollen parent). The new cultivar was discovered from the progeny of the stated cross by B. Frank Brown. Asexual propagation of division was used to increase the number of plants for evaluation and has demonstrated the stability of the combination of characteristics of the new cultivar from generation to generation.

The seed parent 'Manilla Twirl' is characterized by its ovate and relatively short and narrow leaves, russet petioles, its upper surface leaf color of dark green with plae green-grey chevrons along the primary veins, and its lower leaf surface color of light green. The new cultivar distinguishes from 'Manilla Twirl' by its longer and wide leaves, its light pink/orange petioles, and different leaf coloration.

The pollen parent, an unnamed cultivar of the species *Aglaonema panayensis,* is characterized by its oblong leaves which are shorter and narrower than 'Rembrandt', its pink and russet petioles, and its dark green upper surface foliage color with light green chevrons along the lateral leaf veins. When compared with its pollen parent, 'Rembrandt' has ovate leaves which are longer and wider, pink-orange petioles, and a somewhat different foliage pattern and color.

The following observations, measurements and values describe plants of 'Rembrandt' grown in Palm Bay, Fla., under greenhouse conditions which closely approximate those generally used in horticultural practice.

The following traits have been repeatedly observed and are determined to be basic characteristics of 'Rembrandt', which in combination distinguish 'Rembrandt' from other Aglaonema of the same general type.

1. The leaf is larger than either parent.
2. The combination of yellow midrib, yellow spots and gray strips make 'Rembrandt's' pattern unique.
3. 'Rembrandt's' petioles are pink.
4. 'Rembrandt' is free branching giving the plant a wide appearance.
5. 'Rembrandt' has short underground stolons.

All color references below are measured against The Royal Horticultural Society Colour Chart. Colors are approximate as color depends on horticultural practices such as light level and fertilization rate, among others.

The drawing comprises a front perspective color photograph of a plant of 'Rembrandt', with color being depicted as accurately as possible with illustrations of this type. The photo illustrates a plant of 'Rembrandt' in an eight (8) inch pot approximately 45–55 weeks from a plant obtained by division, grown under appropriate conditions.

Origin:

*Seedling.—Aglaonema 'Manilla Twirl'×Agalonema panayensis.*

Classification: Aglanoema hybrida cv. 'Rembrandt'.

Propagation. Asexual production either by tissue culture or division.

Plant: In an 8 inch pot after approximately 40 to 50 weeks of growth under appropriate conditions from a plantlet obtained by division, 'Rembrandt' will be approximately 13 cm. to 16 cm. from the soil surface to the junction of the petioles of the last two (2) unrolled leaves, and approximately 53 cm. to 60 cm. in width. All measurements are based on the above parameters. The ultimate size of 'Rembrandt' will be at least 1 meter tall and 2 meters in width if planted in a sufficiently large container and grown under appropriate conditions.

Stem:

*Growth Pattern.*—The stem is erect in growth and is approximately 1.5 cm. to 2.5 cm. in diameter five (5) cm. above the soil surfae. Internode distance is approximately 1.0 cm to 1.5 cm. three (3) cm. above the soil.

*Color.*—The stem is 27D, 36D blotched with 152A.

Petiole: The following information is based on the 5th expanded leaf from the apex.

*Growth Pattern.*—The petiole has fleshy edges extending from the midrib that will be referred to as wings. The wings are approximately 3 mm. to 5 mm. wide one (1) cm. below the wing tip. The wings extend from the base of the petiole to within approximately 2.2 cm. to 3.5 cm. of the leaf base. The apex of the wings is emarginate. The petiole follows the stem axis but diverges from the axis approximately 10.5 cm. to 12.5 cm. from the leaf base, forming a horizontal distance from the edge of the stem to the leaf base of approximately 4 cm. to 8 cm.

*Dimensions.*—The petiole is curved from its base to the base of the leaf. The petiole is approximately 4mm. to 8 mm. in diameter one-half way between the top of the wing and the base of the leaf.

Color.—The petiole wings and the midrib are 159C with occasional blotches of 137C. Young petioles may also have a blush of 37C.

Leaf:

*Growth Pattern.*—The leaf is ovate with a cuspidate/acuminate apex and a cordate base. The margin is entire. The leaf is asymmetric, with the side of the leaf unrolling first having less surface area and fewer undulations on the leaf margin than the side unrolling last. The leaf is oriented nearly parallel to the stem axis at the time of full unrolling, changing to a slightly more horizontal or subhorizontal orientation as more leaves unroll above it. The midrib droops over the length of the leaf. The leaf blade droops from the midrib to the margin.

*Dimensions.*—For the pot size and growing time indicated, the largest leaf is approximately 25 cm. to 30 cm. long and approximately 11 cm. to 13 cm. wide. An average sized leaf is approximately 23 cm. to 26 cm. long and approximately 9 cm. to 12 cm. wide. The leaf is moderately thick, shiny and slightly ribbed.

*Midrib.*—The midrib is thick and pronounced.

*Primary Veins.*—The primary veins are sunken into the upper surface and protrude out of the lower surface. The primary veins are the same color as the leaf tissue surrounding them.

*Color and Pattern.*—There are numerous areas of the leaf where color is significant, particularly on the upper surface. Upper surface: Darker, generally striped areas from margin to midrib: 139A. Midrib: 159C fading to 150A to slightly yellower than 139A. Gray striping: more gray than 191A, the closest color value. Spots: Initially 159C turning to 150A and then to a color more yellow than 139A. Under surface: Darker areas: 137C. Midrib: 155A. Spots: 157C. (No gray variegation on under surface).

Axillary Breaks: There are approximately 3 to 6 axillary breaks with at least one (1) leaf expanded. Leaves will show color by the 2nd leaf and will have true color and pattern by the 4th leaf.

Inflorescence: Typical of Aglaonema and has no commercial significance. Blooms in spring and fall. No seed has been produced since no efforts to pollinate have been made.

Roots: Thick white roots with finer laterals.

General Observations: 'Rembrandt' is a wide, free branching medium height Aglaonema. The combination of pink petioles, yellow midribs, and leaves with yellow spots and gray stripes imparts a visual experience that is not commercially available in Agalaonemas. 'Rembrandt' is a unique new cultivar.

I claim:

1. A new and distinct cultivar of Aglaonema plant named 'Rembrandt', as described and illustrated.

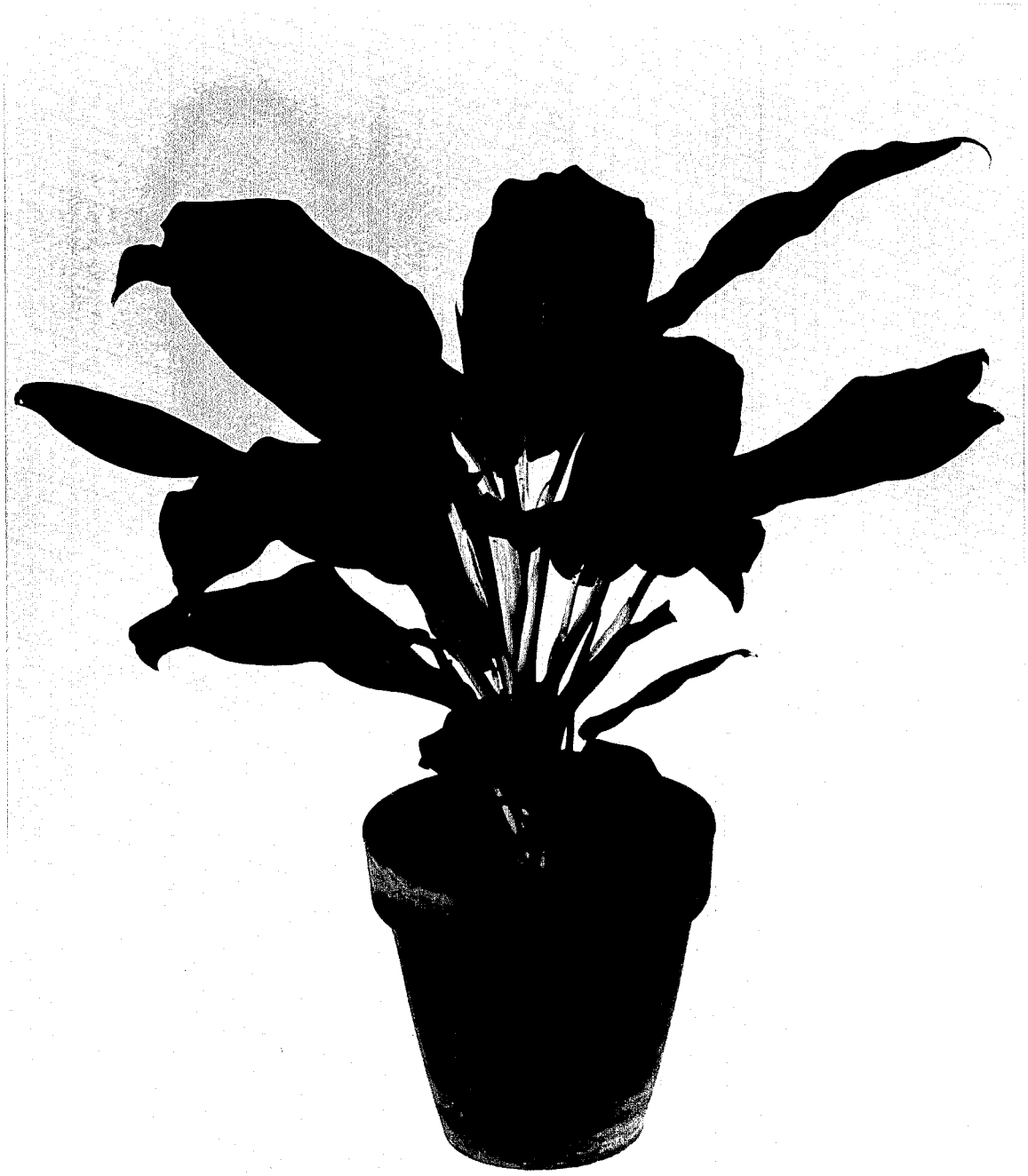

* * * * *